US005837287A

United States Patent [19]

Yarwood et al.

[11] Patent Number: 5,837,287

[45] Date of Patent: Nov. 17, 1998

[54] PROCESS FOR PREPARING SOLID PHARMACEUTICAL DOSAGE FORMS

[75] Inventors: Richard J. Yarwood; Patrick Kearney; Andrew R. Thompson, all of Wiltshire, United Kingdom

[73] Assignee: R P Scherer Corporation, Troy, Mich.

[21] Appl. No.: 437,925

[22] Filed: May 9, 1995

Related U.S. Application Data

[62] Division of Ser. No. 330,936, Oct. 28, 1994, Pat. No. 5,738,875.

[51] Int. Cl.$^{6}$ ................................ A61K 9/00; A61K 9/20

[52] U.S. Cl. ........................... 424/484; 424/485; 424/488

[58] Field of Search .................................... 424/484, 485, 424/488

[56] References Cited

U.S. PATENT DOCUMENTS

| | | | |
|---|---|---|---|
| 4,305,502 | 12/1981 | Gregory et al. | 424/484 |
| 5,039,540 | 8/1991 | Ecanow . | |
| 5,120,549 | 6/1992 | Gole et al. . | |
| 5,188,825 | 2/1993 | Iles et al. | 424/78.1 |
| 5,206,025 | 4/1993 | Courteille et al. | 424/439 |
| 5,298,261 | 3/1994 | Pebley et al. | 424/488 |
| 5,330,763 | 7/1994 | Gole et al. . | |
| 5,372,818 | 12/1994 | Cross et al. | 424/442 |
| 5,382,437 | 1/1995 | Ecanow | 424/499 |
| 5,501,861 | 3/1996 | Makino et al. | 424/464 |
| 5,529,789 | 6/1996 | Lo | 424/473 |
| 5,576,014 | 11/1996 | Mizumoto et al. | 424/435 |
| 5,587,179 | 12/1996 | Gergely et al. | 424/488 |
| 5,631,023 | 5/1997 | Kearney et al. | 424/465 |
| 5,720,974 | 2/1998 | Makino et al. | 424/464 |

FOREIGN PATENT DOCUMENTS

| | | |
|---|---|---|
| 0 081 912 | 6/1983 | European Pat. Off. . |
| 0 450 141 A1 | 10/1991 | European Pat. Off. . |
| 0 578 823 A1 | 1/1994 | European Pat. Off. . |
| 1 548 022 | 7/1979 | United Kingdom . |
| 2 111 423 | 7/1983 | United Kingdom . |
| WO 93/127/69 | 7/1993 | WIPO . |
| WO 94/14422 | 7/1994 | WIPO . |

*Primary Examiner*—Robert H. Harrison
*Attorney, Agent, or Firm*—Nixon & Vanderhye

[57] ABSTRACT

A process for the preparation of an oral solid rapidly disintegrating dosage form of a pharmaceutically active substance which has an unacceptable taste which process comprises forming a solution or a suspension in a solvent of a form of the pharmaceutically active substance which is less soluble in water and more palatable than the form with the unacceptable taste together with a water-soluble or water-dispersible carrier material, forming discrete units of the suspension or solution and removing the solvent from the discrete units under conditions whereby a network of the carrier material carrying a dosage of the less soluble and more palatable form of the pharmaceutically active substance is formed.

2 Claims, No Drawings

PROCESS FOR PREPARING SOLID PHARMACEUTICAL DOSAGE FORMS

This is a Rule 60 Divisional of application Ser. No. 08/330,936, filed 28 Oct. 1994. U.S. Pat. No. 5,738,875.

The present invention relates to a process for preparing solid pharmaceutical dosage forms and, in particular, to a process for preparing an oral solid rapidly disintegrating dosage form of a pharmaceutically active substance which has an unacceptable taste to a human being or to an animal.

Many pharmaceutically active substances are presented for oral administration in the form of tablets, pills or capsules. The tablet, pill or capsule generally has to be swallowed with water so that the pharmaceutically active substance can be absorbed via the gastro-intestinal tract. For some patients swallowing the tablet, pill or capsule is difficult or impossible and this is particularly the case for paediatric patients and geriatric patients. A similar difficulty is often encountered when trying to administer tablets to non-human animals which may be uncooperative in taking tablets, pills or capsules.

Oral solid pharmaceutical dosage forms which rapidly disintegrate in the mouth and methods for their preparation have been proposed in GB-A-1548022 and GB-A-2111423. The solid dosage forms as disclosed comprise an open matrix network carrying the pharmaceutically active substance, the open matrix comprising a water-soluble or water-dispersible carrier material which is inert towards the pharmaceutically active substance. The solid dosage forms are prepared by the sublimation or removal of solvent from a solution or suspension comprising the pharmaceutically active substance and the carrier material. Sublimation or removal of solvent is preferably carried out by freeze drying.

Other methods for the preparation of oral solid pharmaceutical dosage forms which rapidly disintegrate in the mouth are disclosed in U.S. Pat. No. 5,039,540, U.S. Pat. No. 5,120,549, U.S. Pat. No. 5,330,763, PCT/JP93/01631 and PCT/US93/12566.

The solid dosage forms which are produced by these various methods rapidly disintegrate on being placed in the mouth of the patient, thereby delivering the desired dose of the pharmaceutically active substance.

Although the solid dosage forms as described above overcome the problem of swallowing tablets, pills or capsules, the patient will taste the pharmaceutically active substrate as the dosage form disintegrates. For some pharmaceutically active substances the taste, if slightly unpleasant, can be rendered acceptable by the use of sweetening agents or flavouring agents which mask the taste. However, for some pharmaceutically active substances an unpalatable product will still be produced, despite the use of sweetening agents and flavouring agents, which decreases patient compliance.

We have now developed a method for the preparation of an oral solid rapidly disintegrating dosage form of a pharmaceutically active substance which has an unacceptable taste which does not only depend upon trying to mask the unacceptable taste by the use of sweetening agents, flavouring agents and the like.

Accordingly, the present invention provides a process for the preparation of an oral solid rapidly disintegrating dosage form of a pharmaceutically active substance which has an unacceptable taste, which process comprises forming a solution or a suspension in a solvent of a form of the pharmaceutically active substance which is less soluble in water than the form with the unacceptable taste together with a water-soluble or water-dispersible carrier material, forming discrete units of the solution or suspension and removing the solvent from the discrete units under conditions whereby a network of the carrier material carrying a unit dosage of the less soluble form of the pharmaceutically active substance is formed.

By the term "rapidly disintegrating" as used herein is meant that the solid dosage form will disintegrate in water at 37° C. in 60 seconds or less, preferably 5 to 10 seconds or less when tested by the following procedure which is analogous to the Disintegration Test for Tablets, B.P. 1973 and which is described in British Patent No. 1548022:

Apparatus

A glass or suitable plastic tube 80 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve (B.P. 1973 page A136).

A glass cylinder with a flat base and an internal diameter of about 45 mm containing water and not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it.

On oral administration of the solid dosage form of the invention to a patient the pharmaceutical dosage form rapidly disintegrates in the mouth.

The oral rapidly disintegrating solid dosage form of the present invention enables poorly tasting pharmaceutically active substances to be presented in a palatable form without changing the bioavailability of the pharmaceutically active substance relative to an existing marketed solid dosage form containing the more soluble compound. The pharmaceutically active substance is presented as a less soluble form rendering less of the drug to be tasted as the solid dosage form dissolves/disintegrates in saliva.

The pharmaceutically active substance with the unacceptable taste may be presented in less soluble form prior to formation of the said solution or suspension. Alternatively, the pharmaceutically active form may be converted into the less soluble form during the process of the invention, for example during the preparation of the solution or suspension.

The pharmaceutically active substance with the unacceptable taste may be rendered less soluble by conversion of a salt to a free acid or a free base, changing the salt form, formation of a hydrate, or changing the polymorphic form thereof, or by any other suitable means.

The discrete units of the suspension or solution may be in the form of liquid units, for example contained within the pockets of a suitable mould, solid units, for example frozen units, or gelled units where the carrier material readily forms a gel.

The removal of solvent from the discrete units of the solution or suspension comprising the pharmaceutically active substance in its less soluble form and a water-soluble or water-dispersible carrier material is carried out by techniques well known to those skilled in the art.

When the discrete units are in liquid form they will generally be frozen or gelled prior to drying.

The liquid solution or suspension which may be contained within the pockets of a suitable mould is frozen, for example by passing a gaseous cooling medium, such as liquid nitrogen over the mould, or by inserting the mould into a nitrogen spray freezing chamber, or cooling by passing the mould over a cold surface. Once the dosage forms have been frozen, the mould may be stored in a cold store, prior to drying. Frozen discrete units may be dried by freeze drying according to techniques which are well known in the art. The solvent is sublimed in a freeze drying process under a reduced pressure which transforms the solid solvent directly into a vapour. The freeze drying process will generally be carried out in a freeze drying chamber typically operating under a vacuum of 0.1 to 1.0 mBar for a period of time of from 180 to 500 minutes.

Alternatively, frozen discrete units may be dried by a process as described in U.S. Pat. Nos. 5,120,549 and 5,330,763. In this method the pharmaceutically active substance and carrier material dispersed in a first solvent is solidified and the solidified matrix is subsequently contacted with a second solvent that is substantially miscible with the first solvent at a temperature lower than the solidification point of the first solvent, the matrix component being substantially insoluble in the second solvent, the first solvent thereby being removed from the matrix.

Another alternative process for drying frozen discrete units is described in W094/14422. In this process the solvent is removed under conditions whereby the solvent is evaporated from the solid through the liquid phase to a gas, rather than subliming from a solid to a gas as in lyophilization. This is achieved by vacuum drying at a temperature below the equilibrium freezing point of the composition at which point the solvent (such as water) changes phase.

When the discrete units are gelled units, any drying methods can be used which do not affect the properties of the preparations. For example, drying may be carried out at decreased pressure, or by forced-air drying. Drying at decreased pressure is preferably carried out at a temperature of from 25° to 35° C. under a vacuum of −750 mm Hg or less, for 2 to 5 hours, whilst drying using forced-air drying is preferably carried out at a temperature of from 30° to 15° C. for 1 to 6 days.

The solvent used in forming the solution or suspension of the pharmaceutically active substance is preferably water but it may be admixed with a co-solvent, such as alcohol, if it is desired to improve the solubility of the active substance.

The carrier material which is used to form the network containing the pharmaceutically active substance may be any water-soluble or water-dispersible material that is pharmaceutically acceptable, inert to the pharmaceutically active substance and which is capable of forming a rapidly disintegrating network. The preferred carrier material for use in the present invention is gelatin, preferably pharmaceutical grade gelatin.

Other materials may also be used, for example hydrolysed dextrose, dextran, dextrin, maltodextrin, alginates, hydroxyethylcellulose, sodium carboxymethylcellulose, microcrystalline cellulose, corn-syrup solids, pectin, carrageenan, agar, chitosan, locust bean gum, xanthan gum, guar gum, acacia gum, tragacanth, konjac flour, rice flour, wheat gluten, sodium starch glycolate, soy fibre protein, potato protein, papain, horse radish peroxidase, glycine or mannitol.

The suspension or solution prepared according to the process of the present invention is preferably formed into discrete units by introduction into a mould which preferably comprises a plurality of depressions, each depression being of the desired shape and size for the oral dosage form product. The mould preferably comprises a plurality of depressions formed in a sheet of a filmic material which may be similar to the material employed conventionally in the blister packaging of pharmaceuticals. A particularly preferred filmic material for use as a mould in the present invention is described in W094/12142. The desired quantities of the suspension or solution may be filled into the mould using an automatic filling means which delivers a predetermined dose into each of the depressions in the mould.

A covering material may be adhered to the filmic material in the area surrounding the depressions after the removal of solvent from the solution or suspension filling the depressions. The covering sheet is preferably an aluminium foil or aluminium foil laminate which may be adhered to the filmic material around the depressions by, for example a heat sensitive material. The cover sheet may be adhered to the filmic material in a manner such that it can be peeled away by the user to uncover the oral dosage form in the depression in the mould or, alternatively, it may be adapted for the oral dosage forms to be pushed through.

Alternative methods of forming discrete frozen or gelled units of the solution or suspension include solidifying the mixtures in dropwise fashion. For example, the solution or suspension may be passed through one or more holes to form drops, spheres or a spray of small particles which can be solidified by passage through a cold gas or liquid, for example liquid nitrogen. Alternatively, the drops, spheres or spray may be solidified by contact with a chilled liquid which is immiscible with the solution or suspension and which has a density such that the drops either fall through the immiscible liquid as they solidify, or float on the surface of the immiscible liquid.

The suspension or solution prepared in accordance with the process of the present invention may also contain other additional ingredients such as colouring agents, flavouring agents, sweetening agents or preservatives, or fillers such as mannitol or sorbitol which improve the physical properties of the oral dosage form.

The process of the present invention may be used to prepare oral solid rapidly disintegrating dosage forms of various pharmaceutically active substances which have an unacceptable taste. For example, loperamide is incorporated into conventional tablets in the form of its hydrochloride which has an unacceptable taste for formulation into an oral rapidly disintegrating dosage form. However, the use of loperamide in the form of the free base enables a palatable formulation to be produced. Similarly, domperidone is incorporated into conventional tablets in the form of its maleate which has an unacceptable taste for formulation into an oral rapidly disintegrating dosage form. However, the use of domperidone in the form of the free base enables a palatable formulation to be produced.

An advantage of the use of the less soluble forms of the pharmaceutically active substances in the process of the present invention is that the less soluble forms are generally easier to freeze dry, vacuum dry or dry conventionally.

The process of the present invention for making more palatable oral rapidly disintegrating dosage forms obviates the need to use costly drug coating techniques or complexation techniques to mask the taste of the pharmaceutically active substance.

The present invention also includes within its scope the oral solid rapidly disintegrating dosage forms prepared according to the process of the invention.

Accordingly, the present invention includes within its scope an oral solid rapidly disintegrating dosage form of a pharmaceutically active substance which has been rendered more palatable by the process as described above.

The present invention will be further described with reference to the following Examples.

EXAMPLE 1

An oral solid rapidly disintegrating dosage form of loperamide was prepared from loperamide hydrochloride as follows:

| Ingredients | Quantities for 400 units |
|---|---|
| Loperamide hydrochloride | 0.809 g |
| Gelatin | 2.345 g |
| Mannitol | 1.759 g |
| Aspartame | 0.300 g |
| Mint flavour | 0.120 g |
| Sodium hydrogen carbonate | 0.150 g |
| Purified Water | 54.526 g |

The gelatin was added to water in a mixing bowl and heated with mixing to approximately 40° C. The mixture was mixed and homogenized under vacuum until dissolution of the gelatin was complete.

The gelatin solution was added to a mixture of mannitol, sodium hydrogen carbonate and loperamide hydrochloride and the mixture mixed and homogenised until the soluble components had dissolved and the dispersion of the drug particles was complete. The mixture was cooled under vacuum and aspartame and mint flavour added thereto.

The suspension was dosed into blister pockets, frozen and freeze dried to produce the final dosage form.

During the processing the loperamide hydrochloride was converted into the less soluble loperamide free base form by the sodium hydrogen carbonate buffer.

The product had an acceptable taste.

EXAMPLE 2

Domperidone maleate is a poor tasting pharmaceutical compound and when initially formulated as a freeze dried rapidly disintegrating oral dosage form, produced an unacceptable product.

Domperidone was formulated in the form of the free base (which is less soluble in water or saliva than domperidone maleate) into an oral solid rapidly disintegrating dosage form using the following ingredients.

| Ingredients | Weight per Unit |
|---|---|
| Domperidone | 10 mg |
| Aspartame | 0.75 mg |
| Peppermint flavour | 0.15 mg |
| Gelatin | 5.70 mg |
| Mannitol | 5.20 mg |
| Purified water | 128.20 mg |

A solution containing the gelatin and mannitol was prepared and to this were added the aspartame and peppermint flavour. Aliquots of the resulting solution were added to the domperidone powder and a paste formed on stirring. The remainder of the solution was added and homogeneous suspension obtained. The suspension was dispensed in 150 mg aliquots into the pockets of a blister pack, frozen and freeze dried to produce the final dosage form.

The product had an acceptable taste.

We claim:

1. An oral solid rapidly disintegrating dosage form comprising domperidone free base as the pharmaceutically active substance in uncoated and uncomplexed form in a network of a carrier material selected from the group consisting of water-soluble and water-dispersible carrier material.

2. An oral solid rapidly disintegrating dosage form of a pharmaceutically active substance which has an unacceptable taste which has been prepared by a process which comprises forming a system selected from the group consisting of an aqueous solution and a suspension in an aqueous medium of an uncoated and uncomplexed form of the pharmaceutically active substance which is less soluble in water and more palatable than the form with the unacceptable taste together with a water-soluble or water-dispersible carrier material, forming discrete units of the system and removing the aqueous medium from the discrete units under conditions whereby a network of the carrier material carrying a dosage of the less-soluble and more palatable uncoated and uncomplexed form of the pharmaceutically active substance is formed, wherein the pharmaceutically active substance is domperidone which is present in the composition in the form of the domperidone free base.

* * * * *